(12) United States Patent
Sjolund et al.

(10) Patent No.: US 12,370,380 B2
(45) Date of Patent: Jul. 29, 2025

(54) METHODS FOR ADAPTIVE RADIOTHERAPY

(71) Applicant: Elekta Instrument AB, Stockholm (SE)

(72) Inventors: Jens Olof Sjolund, Uppsala (SE); Niklas Gunnarsson, Stockholm (SE)

(73) Assignee: Elekta Instrument AB, Stockholm (SE)

( * ) Notice: Subject to any disclaimer, the term of this patent is extended or adjusted under 35 U.S.C. 154(b) by 234 days.

(21) Appl. No.: 18/254,091

(22) PCT Filed: Dec. 3, 2021

(86) PCT No.: PCT/EP2021/084287
§ 371 (c)(1),
(2) Date: May 23, 2023

(87) PCT Pub. No.: WO2022/117883
PCT Pub. Date: Jun. 9, 2022

(65) Prior Publication Data
US 2024/0001148 A1    Jan. 4, 2024

(30) Foreign Application Priority Data

Dec. 4, 2020 (GB) ...................................... 2019188

(51) Int. Cl.
*A61N 5/10* (2006.01)
(52) U.S. Cl.
CPC ......... *A61N 5/1038* (2013.01); *A61N 5/1031* (2013.01); *A61N 5/1037* (2013.01);
(Continued)
(58) Field of Classification Search
CPC ...... A61N 5/10; A61N 5/1031; A61N 5/1037; A61N 5/1038; A61N 5/1039;
(Continued)

(56) References Cited

U.S. PATENT DOCUMENTS

| 2010/0198101 A1 | 8/2010 | Song et al. |
| 2016/0016007 A1 | 1/2016 | Bharat et al. |

(Continued)

FOREIGN PATENT DOCUMENTS

| WO | WO-2012066494 A2 | 5/2012 |
| WO | WO-2018090091 A1 | 5/2018 |

(Continued)

OTHER PUBLICATIONS

"International Application Serial No. PCT/EP2021/084287, International Search Report dated Mar. 17, 2022", (Mar. 17, 2022), 5 pgs.

(Continued)

*Primary Examiner* — Jurie Yun
(74) *Attorney, Agent, or Firm* — Schwegman Lundberg & Woessner, P.A.

(57) ABSTRACT

The present invention relates to the field of radiation therapy and methods, software and systems for adaptive radiotherapy. There is provided a method for adaptive radiotherapy treatment of a patient comprising receiving a sequence of measurement data of the treatment, the measurements being captured at different time points, mapping measurement data to a representation of a treatment geometry at the time points, using the representation in a dynamical model describing how variables in the representation evolve over time, based on the dynamical model, estimating positions over time of the treatment geometry or selected parts of the treatment geometry, determining a treatment action for the patient at a defined time point using the estimation from the dynamical model and executing the treatment action at the defined time point.

20 Claims, 10 Drawing Sheets

(52) U.S. Cl.
CPC ......... *A61N 5/1039* (2013.01); *A61N 5/1064* (2013.01); *A61N 5/1081* (2013.01); *A61N 5/1084* (2013.01); *A61N 2005/1055* (2013.01); *A61N 2005/1074* (2013.01)

(58) Field of Classification Search
CPC .. A61N 5/1049; A61N 5/1064; A61N 5/1067; A61N 5/1068; A61N 5/107; A61N 5/1081; A61N 5/1084; A61N 5/1047; A61N 2005/1055; A61N 2005/1074
See application file for complete search history.

(56) References Cited

U.S. PATENT DOCUMENTS

| | | |
|---|---|---|
| 2016/0166854 A1 | 6/2016 | Bharat et al. |
| 2017/0216627 A1 | 8/2017 | Brooks et al. |
| 2019/0192880 A1 | 6/2019 | Hibbard |
| 2020/0129784 A1 | 4/2020 | Beriault et al. |
| 2020/0160972 A1 | 5/2020 | Beriault et al. |

FOREIGN PATENT DOCUMENTS

| | | |
|---|---|---|
| WO | WO-2022117883 A2 | 6/2022 |
| WO | WO-2022117883 A3 | 7/2022 |

OTHER PUBLICATIONS

"International Application Serial No. PCT/EP2021/084287, Written Opinion dated Mar. 17, 2022", (Mar. 17, 2022), 7 pgs.

"United Kingdom Application Serial No. 2019188.8, Response filed Jan. 31, 2023 to Search and Examination Report mailed Jun. 2, 2021", 20 pgs.

"United Kingdom Application Serial No. 2019188.8, Search and Examination Report mailed Jun. 2, 2021", 9 pgs.

"United Kingdom Application Serial No. 2019188.8, Subsequent Examination Report mailed Mar. 23, 2023", 5 pgs.

Sharp, Gregory C., et al., "Prediction of respiratory tumour motion for real-time image-guided radiotherapy", Phys . Med. Biol. 49, (2004), 425-440.

METHODS FOR ADAPTIVE RADIOTHERAPY

PRIORITY APPLICATIONS

This application is a U.S. National Stage Filing under 35 U.S.C. § 371 from International Application No. PCT/EP2021/084287, filed on Dec. 3, 2021, and published as WO2022/117883 on Jun. 9, 2022, which claims the benefit of priority to British Application No. 2019188.8, filed on Dec. 4, 2020; the benefit of priority of each of which is hereby claimed herein, and which applications and publication are hereby incorporated herein by reference in their entireties.

FIELD OF THE INVENTION

The present invention relates to methods, computer-readable medium and modules for adaptive radiotherapy for radiation therapy systems and in radiation therapy treatment.

BACKGROUND OF THE INVENTION

Radiotherapy is a therapy using ionizing radiation, often as part of cancer treatment where the intent is to control or kill malignant cells. One form of radiotherapy is brachytherapy, where a radiation source is placed inside or next to the area requiring treatment. Another form of radiotherapy is external beam radiotherapy, which employs a radiotherapy device that creates a radiation beam of particles (photons, electrons, protons and/or other ions) to irradiate a patient. One such radiotherapy device is a Gamma Knife, which irradiates a patient with a large number of low intensity gamma rays that emanate from radioactive sources and converge with high intensity and high precision at a target (e.g., a tumor). External beam radiotherapy also includes linear particle accelerator (linac)-based radiotherapy (e.g., 3D-CRT, IMRT, VMAT) and circular particle accelerators (e.g., cyclotron, synchrotron, and synchrocyclotron).

A linear accelerator uses radio-frequency energy to create a varying magnetic and electrical field in an elongated accelerating chamber—hence a "linear" accelerator. Electrons are fed into the chamber and are accelerated to near light speed. The resulting beam can be used directly as a form of radiation, but it is more usual to direct this to a suitable "target", a block of an appropriate heavy metal such as tungsten. The electron beam impinges on the tungsten block and causes it to emit a beam of x-radiation. The geometry of the electron beam and the tungsten surface are arranged so that the x-ray beam departs perpendicular to the incoming electron beam and can thus be directed towards a patient. The x-ray beam is collimated to a suitable shape and passes through the patient causing tissue damage. By suitable collimation and by moving the linear accelerator around the patient so that it approaches from a range of directions, such systems can minimize the dosage outside the tumor and maximize it within the tumor. One such radiation device is Elekta Unity®. The Elekta Unity® provides real-time visualization during the treatment using MRI (Magnetic Resonance Imaging) scanners (and/or CT (Computed Tomography) scanners).

This offers, for example, real-time adaptive planning for fast dose shaping. Accordingly, it is necessary to quickly and accurately estimate the position of the patient anatomy in relation to the treatment device. This is often done by acquiring medical images at different points in time and relating them to each other by means of image registration. Image registration already plays an important role for adaptive radiotherapy, where a fractionated treatment scheme may be adapted based on re-scans, but is too slow for real-time applications.

In clinical practice, the current state-of-the-art in radiotherapy is to perform so-called online replanning, meaning that the patient is scanned anew and the treatment adapted at each treatment session. However, tumors in thoracic and abdominal areas, such as the lungs or liver, can move considerably during the treatment, primarily due to respiratory motion. To compensate, safety margins are added to the target, at the expense of the surrounding healthy tissue. Elekta Unity offers the possibility of real-time visualization and hence adaptations of the treatment—a true paradigm shift. However, the only active treatments in clinical use are gated or tracked treatments (Keall et al., 2006; McClelland et al., 2013). In gated treatments the radiotherapy beam is only turned on for a fraction of the respiratory cycle, minimizing the effects of respiratory motion but increasing the treatment time. Somewhat more advanced are tracked treatments, where the radiotherapy beam's focus follows the motion of the tumor centroid (Crijns et al., 2012; Bourque et al., 2017). This reduces both the treatment time and the unwanted side-effects of the motion. But, adaptation based on only such geometrical considerations is merely a proxy for a dose-based adaptation, which would yield even greater improvements (Velec et al., 2011; Kontaxis et al., 2015, 2017).

Statistical shape models have been used to model both inter- and intra-patient variations for dose coverage probability studies (David Tilly, et. al. "Dose coverage calculation using a statistical shape model applied to cervical cancer radiotherapy", Physics in Medicine & Biology, 62(10):4140, 2017) and to model and reconstruct respiratory motion (Frank Preiswerk, "Modelling and reconstructing the respiratory motion of the liver", PhD thesis, University of Basel, 2013). Baumgartner et al. (Baumgartner, Christian F., et al. "Autoadaptive motion modelling for MR-based respiratory motion estimation." Medical image analysis 35 (2017): 83-100.) estimated respiratory motion by performing a non-linear dimensionality reduction, aligning the low dimensional embeddings of multiple datasets and identifying respiratory phases.

However, these prior art methods are not capable of forecasting and compensating for patient motions on a sufficiently accurate level, which for example, is an important and crucial component in real-time adaptive radiotherapy and real-time image-guidance in, for example, radiation therapy systems such as Elekta Unity® which include MRI scanners.

SUMMARY OF THE INVENTION

An object of the present invention is to provide more efficient and improved methods, systems, modules and computer-readable medium for adaptive radiotherapy and image-guidance in, for example, radiation therapy systems.

Another object of the present invention is to provide methods, systems, modules and computer-readable medium for adaptive radiotherapy and image-guidance in, for example, radiation therapy systems.

A further object of the present invention is to provide methods, systems, modules and computer-readable medium for adaptive radiotherapy and image-guidance in, for example, radiation therapy systems such as Elekta Unity® which include MRI scanners.

In embodiments of the present invention, it is used in fractionated treatment, where the treatment is delivered over the course of several treatment sessions spread over days and weeks.

In embodiments of the present invention, it is used in real-time radiotherapy and real-time image guidance in radiation therapy systems.

According to an aspect of the present invention, there is provided a method for adaptive radiotherapy treatment of a patient comprising receiving a sequence of measurement data of the treatment, the measurements being captured at different time points, mapping measurement data to a representation of a treatment geometry at the time points, using the representation in a dynamical model describing how variables in the representation evolve over time, based on the dynamical model, estimating positions over time of the treatment geometry or selected parts of the treatment geometry, determining a treatment action for the patient at a defined time point using the estimation from the dynamical model and executing the treatment action at the defined time point.

According to a second aspect of the present invention, there is provided a computer-readable medium having stored therein computer-readable instructions for a processor, wherein the instructions when read and implemented by the processor, cause the processor to receive a sequence of measurement data of the treatment, the measurements being captured at different time points, map measurement data to a representation of a treatment geometry at the time points, use the representation in a dynamical model describing how variables in the representation evolve over time, based on the dynamical model, estimate positions over time of the treatment geometry or selected parts of the treatment geometry, determine a treatment action for the patient at a defined time point using the estimation from the dynamical model; and send instructions for execution of the treatment action at the defined time point.

According to a further aspect of the present invention, there is provided a method for receiving a sequence of measurement data, the measurements being image data sets, the image data sets being captured at number of different time points, and wherein the step of mapping measurement data to a representation of a treatment geometry includes determining/estimating a displacement field for use in the representation of the treatment geometry, the displacement field describing displacement vectors for a number of points in the sets of treatment data, each displacement vector specifying a position of a point in reference to a previous position.

Hence, the present invention is based on the idea of adapting the radiotherapy treatment on the basis of past, or historical, treatment data, such as 2D image data, present treatment data as well as forecasts or predicted events or development in a treatment geometry, such as in a treatment region of a patient. The inputs to the method or system according to the present invention is time-dependent signals and the outputs the control variables, e.g. machine configurations or some proxy thereof, of a treatment system such as a radiation therapy system that includes an MRI scanner, e.g. Elekta Unity®.

In essence, the invention is based on the following components:
i) An encoding procedure or module executing a mapping from an input space to a state space.
ii) A modelling procedure or module executing a dynamical model (or state space model) where the dynamics of the state space variables, i.e. how they evolve over time, are modelled.
iii) A controlling procedure or module executing a determination of control variables (for the treatment system) from the state space variables.

In embodiments of the present invention, the encoding procedure is a machine learning method trained to map an input signal consisting of a sequence of 2D images to a low-dimensional representation of a position over time or a motion of a treatment geometry. Furthermore, the modelling procedure may use machine learning to capture the dynamics in state space variable, for example, a linear Gaussian state space model could be used. The controlling procedure may use a linear-quadratic regulator, model-predictive control or reinforcement learning. The dimensionality of the motion field may differ depending on the intended type of control, e.g. one or two dimensions may suffice for gating and tracking, whereas three dimensions would be appropriate for dose-based adaptation.

In further embodiments, both the encoding procedure and the modelling procedure may use machine learning methods for video prediction and may be trained separately or together. An example of the former would be to predict a trajectory in the latent space using Markov chains or Gaussian processes, or to learn a linear model using dynamic mode decomposition. An example of the latter would be to use a Kalman variational auto-encoder trained on sequences of either images or displacement fields.

The present invention may be used in image-guided radiotherapy or in other applications where the input signal is one-dimensional, for instance in the infrared tracking system the Gamma Knife uses for motion management, or when performing respiratory gating using a spirometric device.

In embodiments of the present invention, the treatment geometry may include a patient anatomy and/or a radiation therapy system or parts of the radiation therapy system.

In embodiments of the present invention, the estimation of positions over time of the treatment geometry or selected parts of the treatment geometry comprises using the dynamical model to make predictions of a motion of the treatment geometry or selected parts of the treatment geometry at a set of future time points.

In embodiments of the present invention, the determination of a treatment action for the patient at a defined time point using the dynamical model's predictions over future time points comprises a control policy designed to minimize an average cost over the future time points, wherein the control policy includes optimal control, dynamic programming, approximate dynamic programming or reinforcement learning. The average cost may include a criteria based on at least one of dose or treatment geometry.

In embodiments of the present invention, the determination of a treatment action for the patient at a defined time point comprises calculating a dose to be delivered to the patient at a defined point of time based on the estimation from the dynamical model and using a cost that includes a deviation between a planned dose and a desired dose and adapting a treatment plan based on the calculated dose. The cost may be a function that returns a single value at each point in time, and that the cost can be made up of various criteria that model e.g. "deviation from ideal dose", "difficulty of delivery" or "sensitivity to noise".

According to embodiments of the present invention, the determination of a treatment action for the patient at a defined time point comprises: calculating a dose to be delivered to the patient at a defined point of time based on the estimation from the dynamical model; and adapting a treatment plan if a predetermined distance function outputs a distance that exceeds a predetermined threshold, where the distance is computed between the calculated dose and the planned dose to be delivered at the defined point of time.

In embodiments of the present invention, a set of candidate treatments plans is updated with the adapted treatment plan.

According to the present invention, the execution of a treatment action comprises selecting a treatment plan among the candidate treatment plans and delivering the calculated dose according to the selected treatment plan.

In embodiments of the present invention, the dynamic model describing how variables in the representation evolve over time comprises a linear Gaussian state space model.

According to embodiments of the present invention, a machine learning model is used in any one or some, or all of the steps of mapping measurement data to a representation of a treatment geometry at the time points; using the representation in a dynamical model describing how variables in the representation evolve over time; based on the dynamical model, estimating positions over time; and determining a treatment action for the patient at a defined time point using the estimation from the dynamical model. The machine learning model may be a neural network.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION OF THE DRAWINGS

The present disclosure includes various techniques to improve and enhance radiotherapy treatment by adjusting radiotherapy device parameters adaptively, for example, in real-time. The technical benefits include reduced radiotherapy treatment time and may result in many apparent medical treatment benefits (including improved accuracy of radiotherapy treatment, reduced exposure to unintended radiation, and the like). The disclosed techniques may be applicable to a variety of medical treatment and diagnostic settings or radiotherapy treatment equipment and devices.

Figure 1:
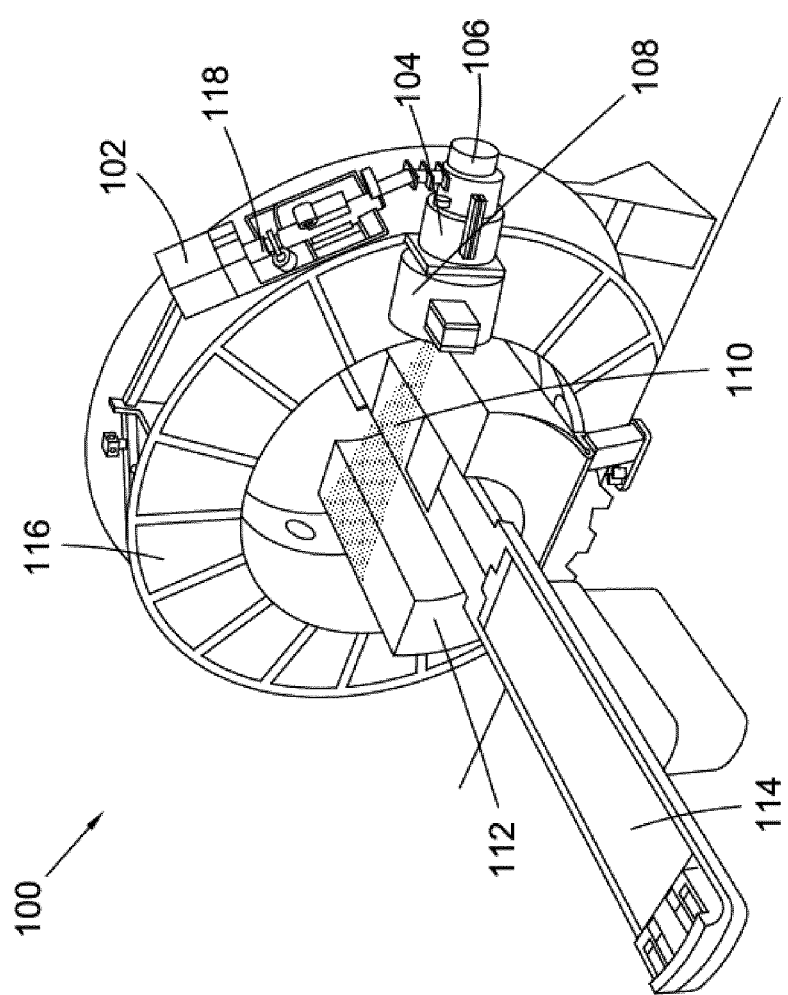
FIG. 1 shows a radiation therapy device in which the present invention can be used.

The present invention is preferably implemented in a device for treating a patient with ionising radiation. FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device. The present invention may also be used in a Gamma Knife system, shown in FIG. 5, and described below.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation 106, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 11 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 13 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 18 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108 before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 18; an RT apparatus processor, which controls the operation of the RT apparatus; and a subject support surface processor which controls the operation and actuation of the subject support surface. The controller is communicatively coupled to a memory, e.g. a computer readable medium.

The linac device also comprises several other components and systems as will be understood by the skilled person. For example, in order to ensure the linac does not leak radiation, appropriate shielding is also provided.

Figure 2:
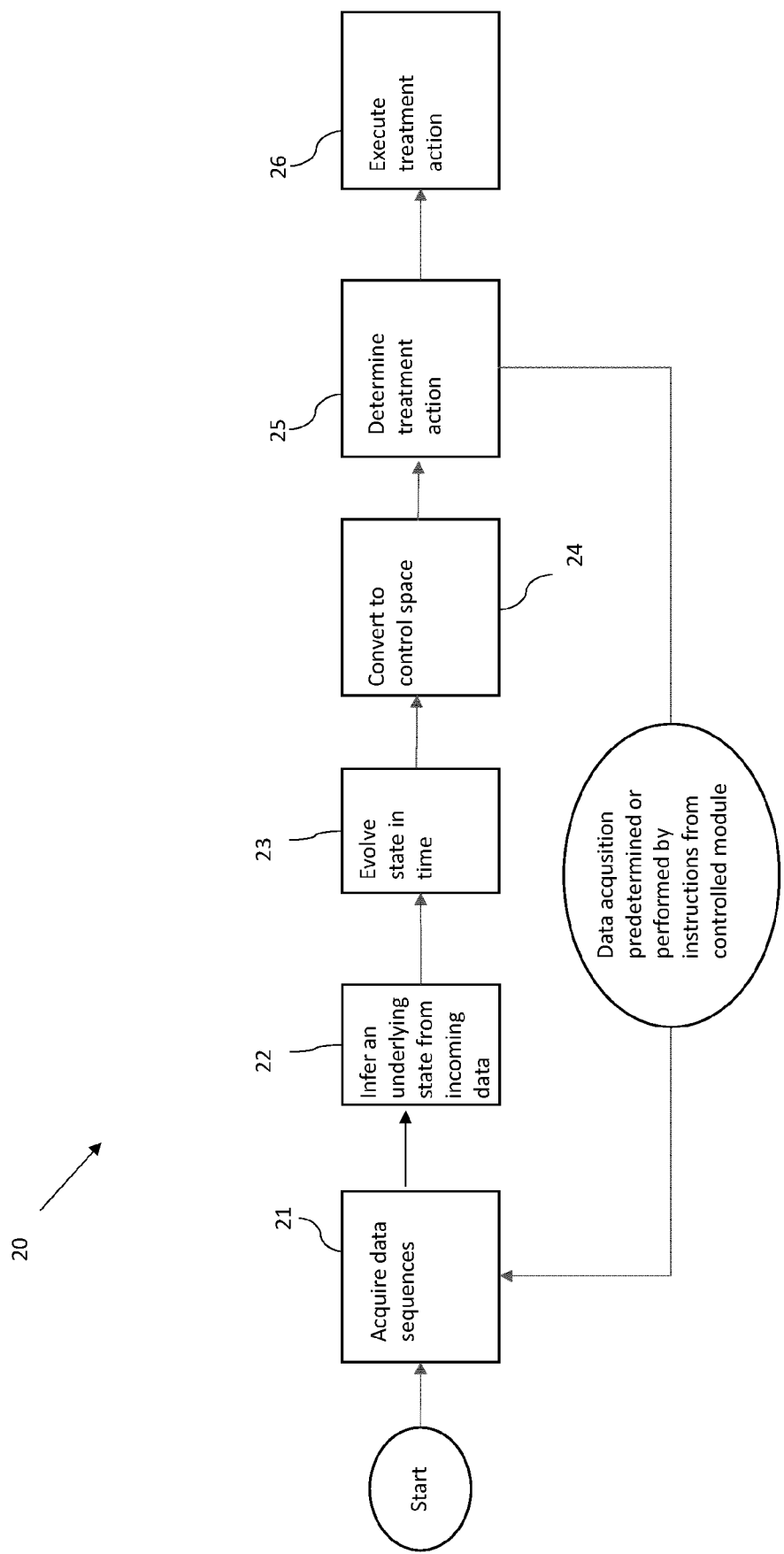
FIG. 2 is a flow chart illustrating an embodiment of the present invention.

With reference now to FIG. 2, a general method 20 according to the present invention will be described. At step 21, sequences of measurement data of a treatment captured at different time points are received. In embodiments of the present invention, the measurement data may be from the infrared tracking system the Gamma Knife uses for motion management, or measurements when performing respiratory gating using a spirometric device. In other embodiments of the present invention, the sequences of measurement data may be image data, such as medical data, are received, for example, a stream of medical images of a patient including a target to be treated with radiation therapy. The medical images may be one or more images of the patient's anatomy for a region of interest (e.g., a target organ, a target tumor or both). Each image, typically a 2D image or slice, can include one or more parameters (e.g., a 2D slice thickness, an orientation, and a location, etc.). For example, an orientation of the 2D slice can include a sagittal orientation, a coronal orientation, or an axial orientation. In an example, 2D slices can be determined from information such as a 3D CBCT or CT, or MRI volume. A pre-processing step can be implemented, for example, some form of dimensionality reduction such as PCA, t-SNE, autoencoder; or some classical computer vision method, e.g. resizing, de-texturize, de-colorize, edge enhancement, salient edge map, local phase, flip, rotate, crop, image registration; or some machine learning method, e.g. a convolutional neural network. Further, it may be some classical preprocessing method for that medical imaging modality: bias-field correction, intensity normalization, distortion correction, denoising.

In step 22, an encoding procedure is performed, where an underlying state is inferred from the measurement, i.e. the incoming measurement data, or in other words, a mapping from the input space X to a state space Z is conducted where the measurement data is mapped to a representation of a treatment geometry. The treatment geometry may be the patient's anatomy as well as how the patient is positioned in relation to the treatment machine, or the treatment machine.

For example, image data of a sequence of incoming image data sets can be mapped to a representation of a motion of an object in the image data over the time period of the sequence. In embodiments of the present invention, the object may be a target tumor.

At step 23, a state space model is applied to the representation of a motion of the object, or the state space Z is evolved in time. The state space model is a model of the dynamics of the state space variables $z_t \in Z$, i.e. how they evolve over time. In embodiments, the state space model is a machine learning method trained to map an input signal consisting of a sequence of 2D images to a low-dimensional representation of the motion.

In embodiments of the present invention, the state space model uses machine learning methods to capture the dynamics:

$$z_{t+1} = f(z_0, \ldots, z_t).$$

In one embodiment of the present invention, the representation in a dynamic model describing how variables in the representation evolve over future time points comprises using a linear Gaussian state space model, where the linear Gaussian state space model is:

$$z_{t+1} = Az_t + \varepsilon_t, \varepsilon_t \sim N(0, \sigma^2),$$

At step 24, a conversion to a control space is performed, i.e. the control variables are determined from the state space variables. A linear-quadratic regulator or model-predictive control may be used. The dimensionality of the motion field may differ depending on the intended type of control, e.g. one or two dimensions may suffice for gating and tracking, whereas three dimensions would be appropriate for dose-based adaptation.

Hence, based on the dynamic model, positions over time of a treatment geometry or part of a treatment geometry can be estimated and at step 25, a treatment action for a patient at a defined time point using the estimated positions over time of a treatment geometry or part of a treatment geometry can be determined. For example, determining a treatment action for the patient at a defined time point may comprise calculating a dose to be delivered to the patient at a defined point of time based on the estimation from the dynamical model and using a cost that includes a deviation between a planned dose and a desired dose. The cost may be a function that returns a single value at each point in time, and that the cost can be made up of various criteria that model e.g. "deviation from ideal dose", "difficulty of delivery" or "sensitivity to noise". In step 26, the treatment action is executed at the defined time point.

A controller module 216, see below with reference to FIG. 7, may determine when image data acquisition in step 21 is to be performed or executed, or alternatively, the image data acquisition in step 21 may be performed at predetermined time points.

Figure 3:
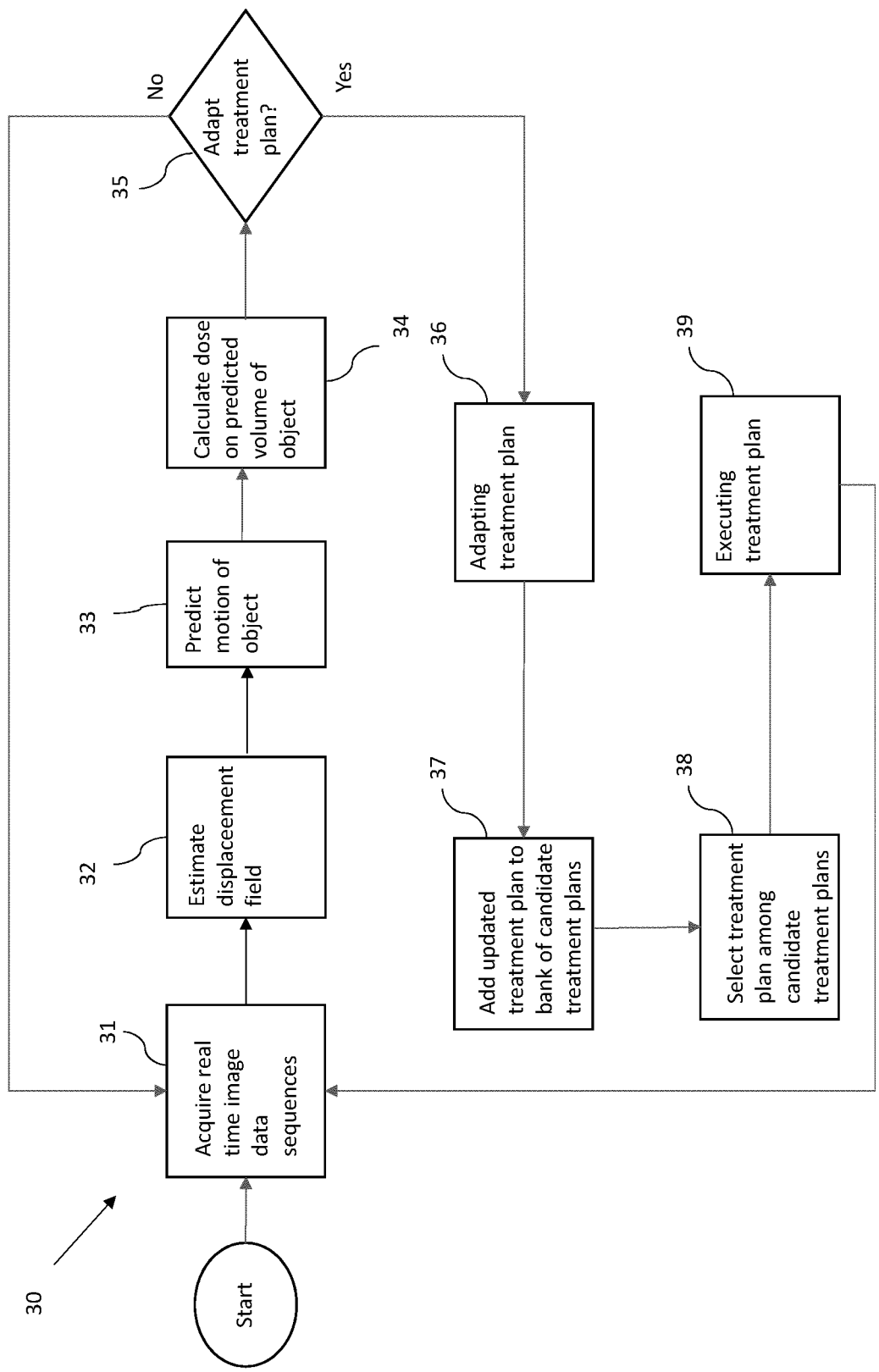
FIG. 3 is a flow chart illustrating an embodiment of the present invention.

With reference now to FIG. 3, an embodiment of a method 30 according to the present invention will be described. This embodiment of the method is preferably used in a radiation device as described with reference to FIG. 1, such as Elekta Unity®.

At step 31, sequences of image data, such as medical data, are received, for example, a stream of medical images of a patient including a target to be treated with radiation therapy. The medical images may be one or more images of the patient's anatomy for a region of interest (e.g., a target organ, a target tumor or both). Each image, typically a 2D image or slice, can include one or more parameters (e.g., a 2D slice thickness, an orientation, and a location, etc.). For example, an orientation of the 2D slice can include a sagittal orientation, a coronal orientation, or an axial orientation. In an example, 2D slices can be determined from information such as a 3D CBCT or CT, or MRI volume. A pre-processing step can be implemented, for example, some form of dimensionality reduction such as PCA, t-SNE, autoencoder; or some classical computer vision method, e.g. resizing, de-texturize, de-colorize, edge enhancement, salient edge map, local phase, flip, rotate, crop, image registration; or some machine learning method, e.g. a convolutional neural network. Further, it may be some classical preprocessing method for that medical imaging modality: bias-field correction, intensity normalization, distortion correction, denoising.

In step 32, an estimation of a displacement field is performed. In embodiments of the present invention, this may include identifying tracking targets (corresponding to pre-selected tracking targets) in the sets of image data captured at different times and estimating a displacement field describing displacement vectors for a number of points in the sets of image data including the tracking regions, wherein each displacement vector specifies a position of a point in reference to a previous position. The tracking of selected tracking regions can be made, for example, using a feature extractor. For example, a discriminative correlation filter that optimizes a correlation filter for a given region may be used. By using a discriminate correlation filter as tracking algorithm, a modality agnostic model can be created. Since the filter is trained and learn from its initial image and it's updated online no modality assumptions have to be made. Other choices of tracking methods are of course possible, e.g. the more traditional Lucas-Kanade (1981) method, or dense based methods, such as Demons, LDDMM, or other (machine learning based for fast execution etc.).

The tracking may use old images, or intermediate results (e.g. confidence maps) and/or vector fields as additional inputs. Update of the feature extractor can be done at fixed interval or dynamically (when some criteria is met), in either case it need not happen on every iteration. The estimation of the displacement field may use additional information from external sources such as ultrasound, respirometry, surface tracking, planar X-ray, CT, 1D MRI, 2D MRI, 3D MRI, camera.

Hence, in step 32, a ground dense motion field or displacement field is produced or created describing displacement vectors for a number of points in a data set, each displacement vector specifying a position of a point in reference to a previous position.

Thereafter, in step 33, a motion prediction is performed of, for example, an object in the image data describing a forecasted or predicted motion of the object over a future time period. In embodiments of the present invention, an encoding procedure is performed, where an underlying state is inferred from the measurement, i.e. the incoming image data, or in other words, a mapping from the input space X to a latent state space Z is conducted. For example, image data of a sequence of incoming image data sets can be mapped to a representation of a motion of an object in the image data over the time period of the sequence. In embodiments of the present invention, the object is a target tumor. A state space model is applied to the representation of a motion of the object, or the state space Z is evolved in time. The state space model is a model of the dynamics of the state space variables, i.e. how they evolve over time. In embodiments, the state space model is a machine learning method trained to map an input signal consisting of a sequence of 2D images to a low-dimensional representation of the motion. The state space model may use machine learning methods to capture the dynamics:

$$z_{t+i} = f(z_0, \ldots, z_t).$$

In one embodiment of the present invention, the representation in a dynamic model describing how variables in the representation evolve over future time points comprises using a linear Gaussian state space model, where the linear Gaussian state space model is:

$$z_{t+1} = Az_t + \varepsilon_t, \varepsilon_t \sim N(0, \sigma^2),$$

A conversion to a control space is performed, i.e. the control variables is determined from the state space variables. A linear-quadratic regulator or model-predictive control may be used. The dimensionality of the motion field may differ depending on the intended type of control, e.g. one or two dimensions may suffice for gating and tracking, whereas three dimensions would be appropriate for dose-based adaptation.

At step 34, a dose is calculated based on the predicted motion of the object for a defined time point in the future. Hence, a radiotherapy processing computing system 202 can be configured upon instruction calculate dose delivery to a subject (e.g., from one or more MR images), for example, within a given fraction in real time or a future time point and modify parameters of the radiotherapy device for subsequent doses based on the calculated dose delivery to an expected dose delivery.

In step 35, a decision is made whether to adapt a current treatment plan based on the calculated dose delivery. For example, a predetermined distance function outputs a distance that exceeds a predetermined threshold, where the distance is computed between the calculated dose and the planned dose to be delivered at the defined point of time. In embodiments, it may be evaluated whether there is a need to modify treatment device parameters in real time within a given fraction or at a future time point. In an embodiment, it may be compared, at a particular time within a fraction, a patient anatomy and/or an amount of dose to be delivered to a target with the expected anatomy and/or dose calculated. If the treatment plan is to be updated to adapted, in step 36, based on a deviation between the anatomy and/or amount and the expected anatomy and/or amount, the parameters of the radiotherapy device may be modified, that is whether to increase, decrease, or make no adjustments to the radiotherapy device parameters based on the deviation. If it is decided not to adapt the treatment plan, the procedure may return to image data acquisition in step 31.

In step 37, the adapted treatment plan is added to a set or bank of candidate treatment plans. For example, a database 220 or a storage device 210 of a radiotherapy computer system or structure 202 may a set of radiation therapy candidate treatment plans (e.g., training data, such as paired prior patient data, such as diagnosis, prescription, treatment planning strategies, and intra-fraction radiotherapy device adaptation strategies and device adjustment amounts, and the like).

At step 38, a treatment plan may be selected and, in step 39, the selected treatment plan is executed by instructing the radiotherapy device, for example, MR linac described with reference to FIG. 1 to irradiate the patient in accordance with the treatment plan. The procedure may return to image acquisition in step 31 thereafter.

Figure 4:
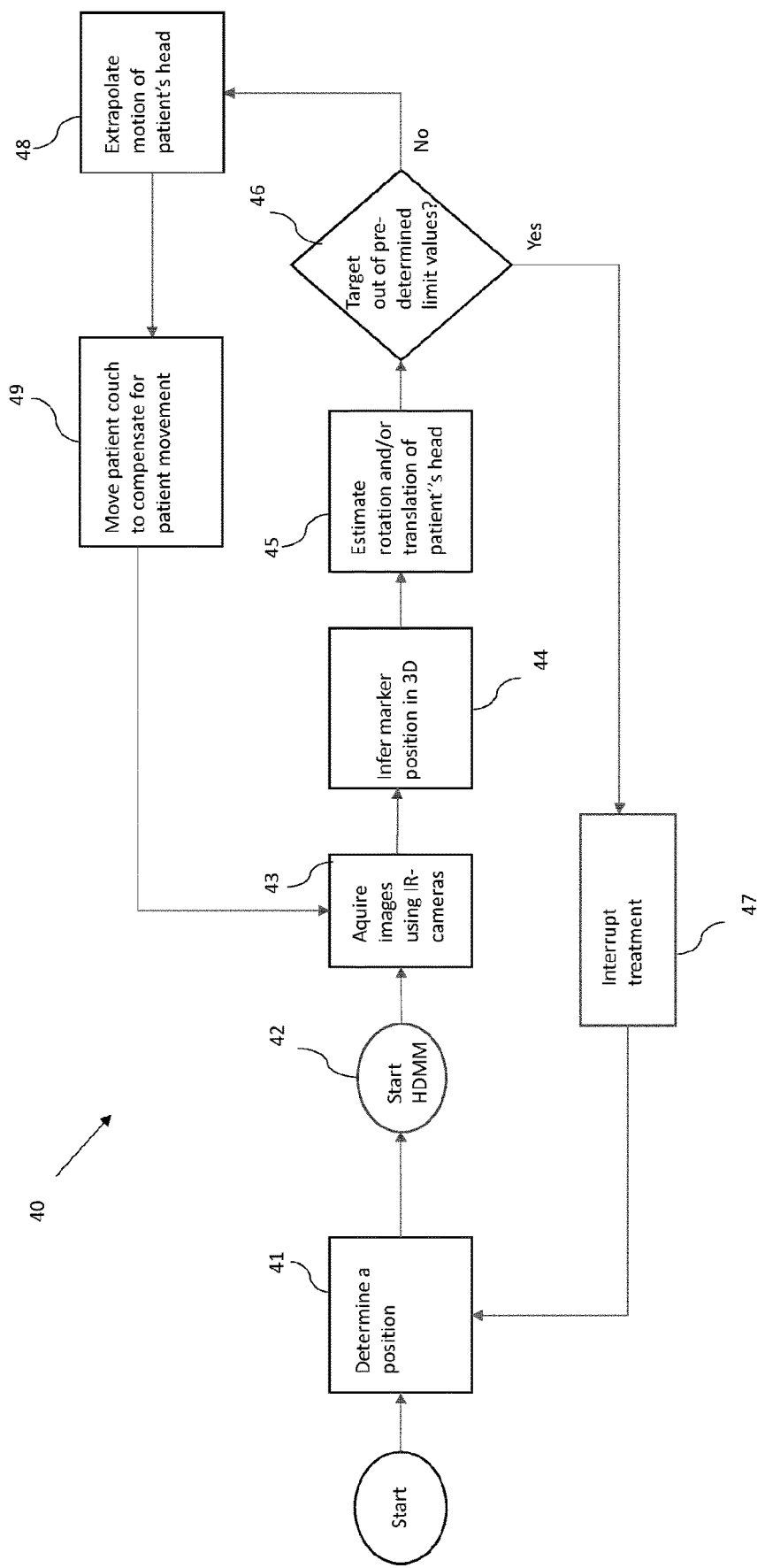
FIG. 4 is a flow chart illustrating a further embodiment of the present invention.
Figure 5:
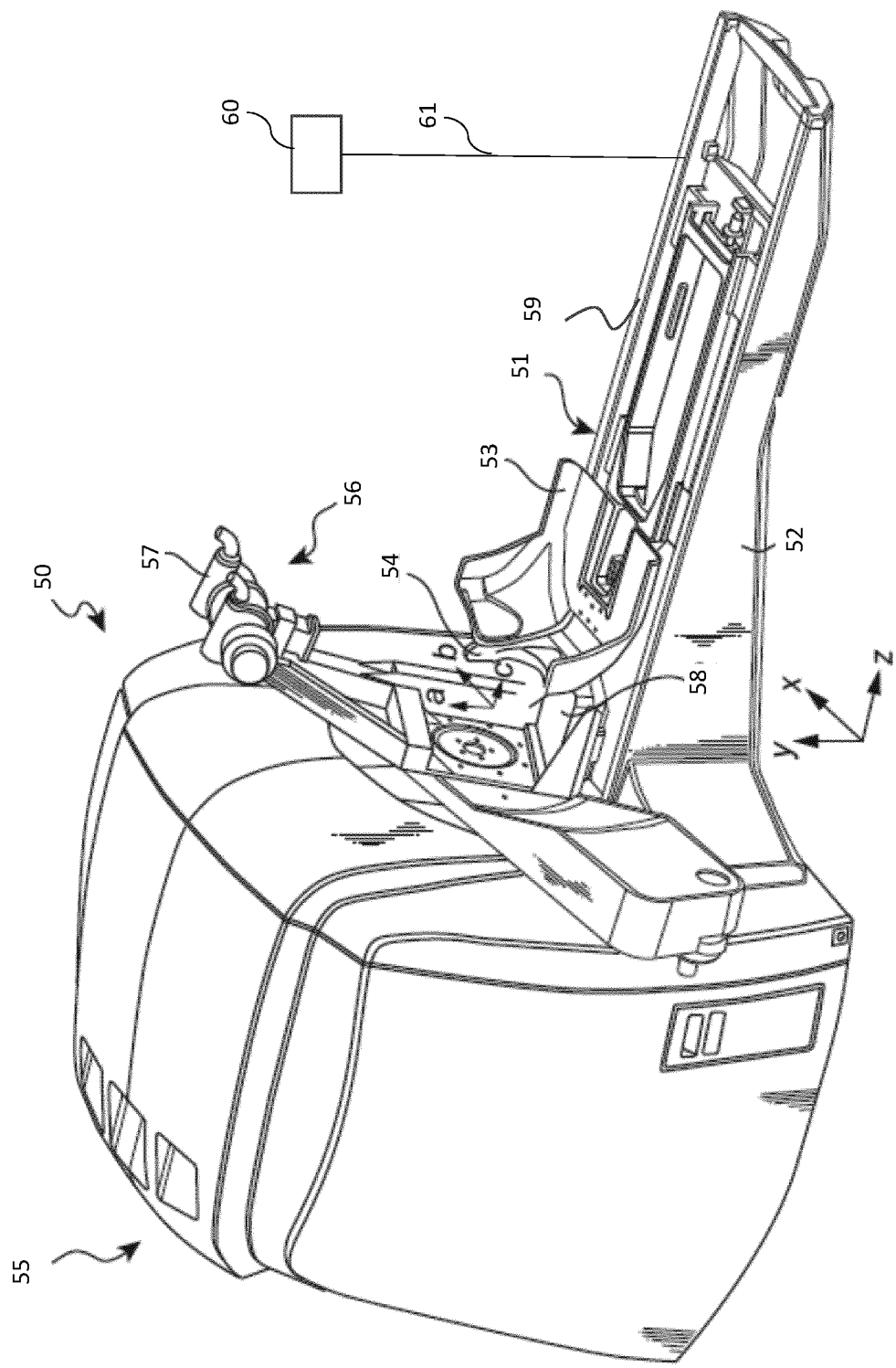
FIG. 5 shows another radiation therapy device in which the present invention can be used.

With reference now to FIG. 4, an embodiment of a method 40 according to the present invention will be described. This embodiment of the method is preferably used in a High Definition Motion Management (HDMM) system using a radiation device such as Leksell Gamma Knife® Icon™. With reference to FIG. 5, a Gamma Knife® system is generally described. This system is capable of monitoring patient movements with sub-millimeter accuracy in 3D and enables the use of non-rigid fixations.

The High Definition Motion Management (HDMM) system consists of an infrared stereoscopic camera, a set of reference markers, and a patient marker. The system continuously tracks the movements of the patient during treatment with non rigid fixations. If large movements are detected sources are moved to an off position and the operator is alerted. The treatment can be resumed again when the patient has returned to the initial position.

The infrared camera is mounted onto an arm on a patient couch. This arm can be folded up when the HDMM system is used and folded down to stow away the camera when not in use. The camera tracks a number of markers attached to a mask adapter worn by the patient. These markers define a reference coordinate system in which the patient movements are measured.

First, at step 41, a position of a target is determined, for example, the position of a target inside the skull of the patient is determined using a cone-beam CT and the position is calculated in CBCT images. Thereafter, the dose plan can be translated if required.

In step 42, the High Definition Motion Management (HDMM) system is started, and in step 43 images are simultaneously acquired using IR cameras, in preferred embodiments, a stereo pair of infrared cameras are used. The cameras track at a frequency of 20 Hz a number of markers attached to the mask adapter. These markers define a reference coordinate system in which the patient movements are measured. This reference system is necessary to reduce noise and any effect of camera movements.

In step 44, a nose marker position in 3D is estimated or determined using the infrared images, and based on this, at step 45, a rotation and/or translation of the patient's head is estimated.

In step 46, it is determined whether the position of the target has changed, i.e. whether the target has been moved, and if the position change is within predetermined limits values. For example, if the target is more than 1 mm off or away from its initial position for more than 10 seconds, the procedure may determine that the target is out of the predetermined limit values. If yes, the procedure moves on to step 47 where the treatment is interrupted, and the operator is alerted. The treatment can be resumed again when the patient has returned to the initial position and, thereafter, the procedure returns to step 41, where a new position of a target is determined, for example, the position of a target inside the skull of the patient is determined using a cone-beam CT and the position is calculated in CBCT images.

On the other hand, if the position of the target is within the predetermined limit values, the procedure proceeds to step 48 where the motion of the patient's head is extrapolated using the methods of the present invention and in step 49 the patient's couch is moved to compensate for the motion. Thereafter, the procedure returns to step 43.

With reference now to FIG. 5, a radiation therapy system 1 for which the present invention is applicable comprises a radiation unit 55 and a patient positioning unit 51. In the radiation unit 55, there are provided radioactive sources, radioactive source holders, a collimator body, and external shielding elements. The collimator body comprises a large number of collimator channels directed towards a common focus, in a manner as is commonly known in the art.

The collimator body also acts as a radiation shield preventing radiation from reaching the patient other than through the collimator channels. Examples of collimator arrangements in radiation therapy systems applicable to the present invention can be found in WO 2004/06269 A1, which is hereby incorporated by reference.

The patient positioning unit 51 comprises a rigid framework 52, a slidable or movable carriage 53, and motors (not shown) for moving the carriage 53 in relation to the framework 52. The carriage 53 is further provided with a patient bed (not shown) for carrying and moving the entire patient. At one end of the carriage 53, there is provided a fixation arrangement 54 for receiving and fixing a stereotactic fixation unit (not show), either directly or via an adapter unit (not shown), and thereby preventing the stereotactic fixation unit from translational or rotational movement in relation to the movable carriage 53. The patient can be translated using the patient positioning unit 51 in the coordinate system of the radiation therapy system 50 or the patient positioning unit 51, along at least in the three orthogonal axes x, y, and z shown in FIG. 1. The patient can, in some embodiments, also be translated along, for example, a rotational axis.

An imaging system 56 for capturing images of a patient, for example, in connection with treatment planning or treatment is arranged or located at the radiation unit 55, for example, a cone beam computed tomography (CBCT) system.

The imaging system 56 includes an X-ray source 57 and a detector 58. The X-ray source 57 and detector 58 are arranged to rotate around a rotation axis c (see FIG. 1) of a coordinate system (a, b, c) of the imaging system 56 to capture images of a patient located on the patient bed 59 at different angles. Ideally, the X-ray source 57 and the detector 58 rotate around the z-axis of the patient positioning unit 51, which is aligned with the rotation axis c of the imaging system 56. However, in practice, there are, for example, alignments errors due manufacturing tolerances leading to a misalignment between the coordinate system of the patient positioning unit 51 and the imaging system 56 and accordingly the c-axis is not aligned with the z-axis.

In computed tomography, a three-dimensional image is generated by rotating the imaging system around the object in very small steps (e.g. <1°) around a single axis of rotation while taking a series of two-dimensional X-ray images. In other applications, the object is rotated around the imaging in small steps. Normally, the imaging device or the object is rotated, for example, 180° or 360° around the object or imaging device, respectively. Afterwards, a final three-dimensional image can be numerically reconstructed based on the two-dimensional images and can be displayed either as a series of sectional images or a three-dimensional image.

Further, an infrared stereoscopic cameras 60 is mounted onto an arm 61 on the couch. This arm can be folded up when the HDMM system is used and folded down to stow away the camera when not in use. The camera tracks at a frequency of 20 Hz a number of markers attached to the mask adapter of the patient. These markers define a reference coordinate system in which the patient movements are measured. This reference system is necessary to reduce noise and any effect of camera movements.

As can be understood from FIG. 5, the described embodiment concerns a radiation therapy system for providing gamma radiation therapy to a target volume in the head of human patient. Such therapy is often referred to as stereotactic surgery. During therapy, the patient head is fixed in a stereotactic fixation unit, for example, using a bite-block and a fixation unit in the form of a stereotactic head frame, which comprises engagement points adapted for engagement with the fixation arrangement 54 of the radiation therapy system. Thus, during the stereotactic surgery, the head of the patient is fixed in the stereotactic frame, which in turn is fixedly attached to the patient positioning system via the fixation arrangement 54. During movement of the treatment volume in the head of the patient in relation to the radiation focus, e.g. along the three axes x, y, and z shown in FIG. 1, the entire patient is moved. Thus, there is no relative to movement between the head frame and the carriage 53 of the patient positioning system 51.

The present application relates generally to spatiotemporal imaging, and the techniques disclosed herein have applications in, for example cardiac diagnostics, surgical guidance, and radiotherapy monitoring. In this application, the temporal motion is described by identifying the underlying dynamics. In implementations of the present disclosure, the underlying dynamics can be derived based only on images, e.g based on sequential images. The resulting model maps the inputs to a low-dimensional latent space wherein a linear relationship between a hidden state process and an observed latent process holds. For this, a conditional variational auto-encoder (CVAE) is used to nonlinearly map the higher dimensional image to a lower-dimensional space, and the dynamics may be modelled with a linear Gaussian state-space model (LG-SSM). The model may be a modified version of the Kalman variational auto-encoder and is end-to-end trainable. The weights of the model, both in the CVAE and LG-SSM, are simultaneously updated by maximizing the evidence lower bound of the marginal likelihood. The motion is explained with a spatial transformation from one image to another. This results in sharper reconstructions and the possibility of transferring auxiliary information, such as segmentations, through the image sequence.

An advantage of the techniques disclosed herein is that the dynamics in a medical image time series may be derived based only on the images themselves. According to implementations, an aim is to learn a parameterized function, h, such that the image yt at time t is described by the dynamical system:

$$yt = h(y_{1:t-}) + \epsilon_t \quad (1),$$

where y_(1:t−1)=y_1, . . . y_(t−1) are the previously observed images and $\epsilon t$ is noise. This representation makes it possible to predict $\hat{y}_t = h(y_{1:k})$ based on observations up to time k, i.e. to impute (t<k), filter (t=k), or extrapolate (t>k) images.

Temporal medical images contain high-dimensional data where the dynamics, due to cyclic and deformable motion, are nonlinear. While the linear assumption is preferable for several reasons, including tractable filtering and smoothing posteriors, it is inappropriate for the raw image series. Techniques of the present disclosure comprise reducing the high-dimensional data to a low-dimensional latent space wherein the linearity assumptions are valid. This can be achieved by combining techniques from generative and dynamic modelling and training the model end-to-end. This is in contrast to prior techniques of motion modelling, which rely on surrogate signals such as EIT electrodes and compression bands, or other side information such as from X-ray tracking of implanted markers or surface tracking. These prior methods are limited to the requirement of this side information. In implementations of the present methods, the dynamics are modelled as a first-order Markov process in order to increase prediction length.

Implementations of the present disclosure comprise making use of the Kalman variational auto-encoder, an unsupervised model for high-dimensional sequential data that, most likely, undergoes nonlinear dynamics. Higher-dimensional observed images, $y=\{y_t\}_{t=1}^T$ may be non-linearly embedded into a lower-dimensional space using a variational auto-encoder. The dynamics of the lower-dimensional features, $x=\{t_x\}_{t=1}^T$ are modeled with a linear Gaussian state-space model based on a state-space process $z=\{t_z\}_{t=1}^T$. The variational auto-encoder and the linear Gaussian state-space model, and then how those are combined into the framework of Kalman VAE, are discussed below and elsewhere herein.

Similar to traditional auto-encoders, variational auto-encoders (VAEs) embed the input y in a lower-dimensional latent space x using an encoder, $E_\phi$ and reconstruct the original input with a decoder, $D_\theta$. They differ in that VAEs are generative and reconstruct the data distribution $p_\theta(y)$ instead of a single sample y. In this case the true posterior $p_\theta(x|y)$ is intractable. By approximating the variational posterior as a multivariate Gaussian, $q_\phi(x|y) = N(x|\mu_{enc}, \Sigma_{enc})$ where $\mu_{enc}$ and $\Sigma^{enc}$ are the outputs from the encoder, it is possible to sample from the variational approximation. From the KL divergence between the approximate and the true posterior we can obtain a lower bound on the true likelihood $$\log p(y) \geq E\left[\log p(y|x) + \log \frac{p_\theta(x)}{q_\theta(x|y)}\right], \quad (2)$$

where the prior over the latent space is usually chosen to be a multivariate Gaussian $p_\theta(x) = N(x|0,I)$. This lower bound is called the evidence lower bound (ELBO) and can be estimated by sampling.

In a VAE, each sample, $x_t \in R^L$, from the approximate posterior is normally distributed with mean, $\mu^{enc}$, and covariance $\Sigma_{enc}$. If Gaussian noise is assumed, it follows that the state-space vector, $z_t$ in the present linear state-space model also follows a normal distribution. More precisely, a linear Gaussian state-space model (LG-SSM) can be described as:

$$p(z_t|z_{t-1}) = N(z_t|Az_{t-1}, Q),$$

$$p(x_t|z_t) = N(x_t|Cz_t, R), \quad (3)$$

where Q and R are covariance matrices for the process and measurement noise, respectively. Given an initial guess $z_1 \sim N(z_1|\mu_1, P_1)$, the joint probability distribution can be expressed using the where Q and R are covariance matrices for the process and measurement noise, respectively. Given LG-SSM model (from (3)), $$p(x, z) = p(x|z)p(z) = p(z_1) \prod\_(t=1)^\wedge Tp(x_t|z_t) \prod_{\{t=2\}}^{T} p(z_t|z_{t-1}). \quad (4)$$

Given observations x the mean and covariance of the state-space variables is analytically tractable using a Kalman filter, $\mu_{t|t}$, $P_{t|t}$, and a Rauch-Tung-Striebel (RTS) smoother (Rauch et al., 1965), $\mu_{t|T}$ $P_{t|T}$.

A Kalman VAE uses a VAE to reduce the dimension of the image time series distribution wherein the dynamics are represented linearly using an LG-SSM in the latent space. The goal is to describe the dynamics of the system in the latent space with an LG-SSM and use the decoder to reconstruct the image time series. Similar to a regular VAE, the ELBO can be derived from the KL divergence between the approximate and true posterior. In a Kalman VAE the approximate posterior is given by $$q\_(\phi,\gamma)(x,z,|y) = p\_\gamma(z|x)q\_\phi(x|y), \quad (5)$$

and the true posterior can be rewritten as $$p_{\theta,\gamma}(x,zy) = p_\theta(y|x)p\_\gamma(x,z). \quad (6)$$

For a single time series $\gamma = \{yt\}_{t=1}^T$ the ELBO is given by $L_{(\phi,\theta,\gamma)}^{KVAE}$ $$L_{(\phi,\theta,\gamma)}^{KVAE} = E_{q\phi(x|y)}[\log p\_\theta(y|x)/q\_\phi(x|y)) + E\_p\_\gamma(z|x)[\log p\_\gamma(x,z)/p\_\gamma(z|x)]] \quad (7)$$

where $\phi$ and $\theta$ are the encoder and decoder parameters, respectively, and $\gamma = A, C, R, Q, \mu_1, P_1$ are the LG-SSM parameters. It is possible to sample (x⁻, z⁻) by first sampling $x^- \sim q_{\theta(x|y)}$ and then conditionally sampling $z^- \sim p\_\gamma(z|x^-)$. Notice that $p\_\gamma(z|x^-)$ is tractable using the Kalman smoother algorithm and the joint distribution $p\_\gamma(x,z)$ is given by (4). With a re-parameterization trick (Kingma and Welling, 2014) the model can be trained end-to-end to minimize the negative ELBO using e.g. stochastic gradient descent.

Figure 6A:
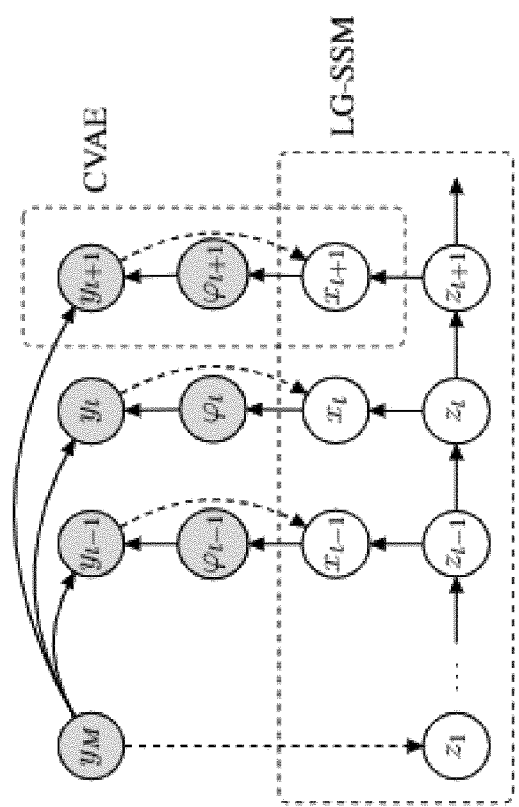
FIG. 6a and FIG. 6b show an illustration and a graphical representation respectively of a model according to the present invention.
Figure 6B:
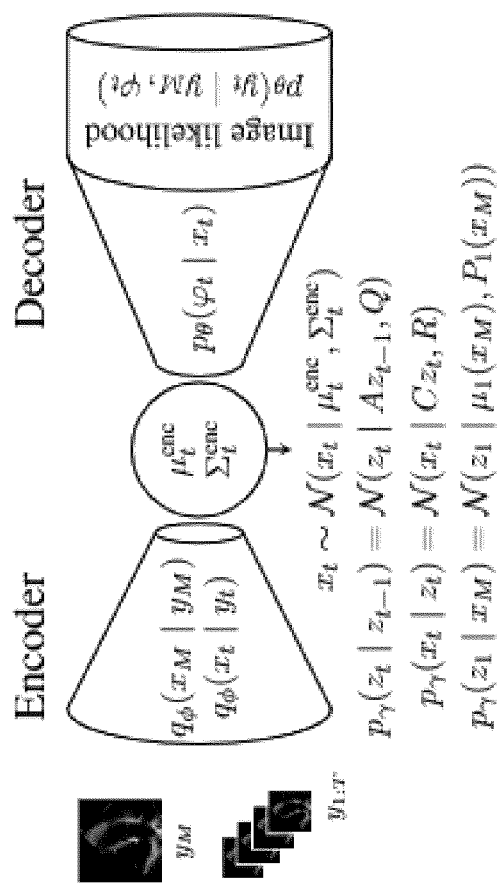

FIG. 6a illustrates the model, and FIG. 6b is a graphical representation of the model. Similar to a Kalman VAE, a lower-dimensional linear-Gaussian state-space model is learnt from data, but unlike a Kalman VAE, the present model operates on image transformations $\varphi_t$ and not images.

The dynamics of the model are driven by the transformation $\varphi_t$ with respect to the spatial information in $y_M$. To include the spatial information of $y_M$ a modified Kalman VAE is sued, where the mappings to and from the latent representation are given by a conditional variational auto-encoder (CVAE), conditioned on the moving image yM. The motion model in the latent space is modeled with an LG-SSM. Here, we condition the initial state prior with the latent representation, $x_M$ of the moving image, such that $p_\gamma(z_1|x_M)$= $N(z_1|\mu_1(x_M), P_1(x_M))$. For this, we use a fully connected neural network to estimate the mean and variance of this distribution. The parameters of our model can be jointly updated by maximizing the ELBO, $L(\phi,\theta,\gamma)$ $$L(\phi,\theta,\gamma)=E_{q_\phi(x,x_M|y,y_M)}[[\log p_\theta(y|x,y_M)/q_\phi(x,x_M|y,y_M)+ E_-(q_\phi(x,x_M|y,y_M))\log p_-\gamma(x,z|x_M)/p_\gamma(z|x,x_M)]], \quad (9)$$

where the ELBO contains of one VAE-part and one LG-SSM-part. For the VAE-part, the generative model is given by $p_\theta(y|x,x_M)=\Pi_{t=1}^T p_\theta(y_t|x_t,y_M)$ and the posterior $q_\phi(x, x_M|y,y_M)=q_\phi(x_M|y_M)\Pi_{t=1}^T q_\phi(x_t|y_t)$. In the LG-SSM part the prior is given by $p_\gamma(x,z|x_M)=p_\gamma(z_1|x_M)\Pi_{t=2}^T p_\gamma(x_t|z_t)\Pi_{t=2}^T p_\gamma(z_t|z_{t-1})$ and the exact conditional posterior $p_\gamma(z|x,x_M)= \Pi_{t=1}^T p_\gamma(z_t|x,x_M)$ can be obtained with RTS smoothing.

In the Kalman VAE the likelihood is assumed to come from some parametric family of distributions, parameterized by the decoder network $D_\theta(x_t)$. Instead of modeling the likelihood of the image intensity, the motion is modelled, i.e. the likelihood of the image transformation $\varphi_t$. Modeling the image transformations enables transferring auxiliary information, such as segmentations, from one image domain to another. Accordingly, in implementations of the present disclosure, one or more images input into the model may be segmented images which contain information regarding characteristics of the patient anatomy shown in the images. For example, a segmented image may comprise areas characterised as bone, lung tissue, tumour tissue, etc. From this segmentation information present in the input images, the tumour position can be identified in the image.

From the decoder we can estimate the likelihood of $\varphi_t$ $$p_\theta(\varphi_t|x_t=N(\varphi_t(\varphi_t|\mu_t^{dec},\Sigma_t^{dec})$$

as a multivariate Gaussian distribution, i.e. the decoder outputs $\mu_t^{dec}$ and $\Sigma_t^{dec}$. A common disadvantage of image-based VAEs is blurry reconstructions due to the restrictive assumption of a Gaussian likelihood. High frequencies, like sharp edges and fine details in the images are often missed in the reconstructions. In the space of image transformations, on the other hand, Gaussian assumptions are quite reasonable. The image likelihood may then be estimated as a noisy observation of the transformed image, $y_M\varphi_t$, i.e.

$$p_\theta(y^t|y_M,\varphi_t)=N(y_t|y_M\circ\varphi_t,\sigma_t^2 I),$$

for some noise $\sigma_t$.

The EchoNet-Dynamic dataset (Ouyang et al., 2020) was used to test the disclosed methods experimentally. The dataset consists of 10030 2D ultrasound echocardiogram time series with 112×112 pixel frames. The time horizon was fixed to 50 time steps (T=50), which corresponded to 1 second and approximately included one cardiac cycle. One sequence per time series was extracted and its start position was selected randomly. Sequences shorter than the fixed horizon were removed (315). 7220 sequences were allocated for training, 1237 for testing and 1258 for validation. The image intensity was normalized to [0, 1] for all images.

The model was evaluated using three metrics, the Dice coefficient (Dice, 1945), the percentage of nonpositive Jacobians (Jacobian determinants), and the execution time. The data sequence included human expert segmentation of the left ventricle at two different time points. The image was used for the first human expert segmentation as moving image $y_M$, and estimated the transformation for the sequence, including the time step for the other human expert segmented image. The quality of transformation was measured with the Dice coefficient, the overlap between the human expert segmentation $S_t$, and the estimation $S_M\circ\varphi_t$ $$\text{Dice} = 2\frac{|S_t \cap (S_M \circ \varphi_t)|}{|s_t| + |S_M \circ \varphi_t|},$$

where a perfect overlap is indicated with a Dice coefficient of 1, and 0 for no overlap. The percentage of non-positive elements in the Jacobian is an indicator of how topology-preserving the transformation is, e.g. if $|J_\varphi(p)|>0$ for all points p the transformation $\varphi$ is diffeomorphic. The Jacobian, $|J_\varphi|$ is defined by $$|J_\varphi| = \begin{vmatrix} \frac{\partial \varphi_x}{\partial x} & \frac{\partial \varphi_x}{\partial y} \\ \frac{\partial \varphi_y}{\partial x} & \frac{\partial \varphi_y}{\partial y} \end{vmatrix}$$

The encoder used consists of downsampling convolutional levels with 16, 32, 64 and 128 filters respectively, where the feature maps at each level are first downsampled using a 2-stride convolutional layer followed by a batch normalization and a leaky ReLU activation function. Furthermore, two 1-stride convolutional layers were used with residual connections before the feature map is downsampled to the next level. The output of the last level is flattened and two dense layers are used—one for the mean, $\{(\mu_t^{enc})\}_{t=1}^T$ and one for the variances, $\{(\sigma_t^{enc}\}_{t=1}^T$.

In the LG-SSM, a dimension of 16 is used for observations, $x_t \in R^{16}$, and 32 for the state space, $Z_t \in R^{32}$. The mean and variance of the initial prior was estimated with a 3 layer fully connected neural network with 16, 16 and 32 units.

The decoder layers mirror the encoder with the same filter sizes and residual connections at each level. The decoder estimates $\mu_t^{dec}$, the mean of the transformation likelihood, and we used a fixed covariance $\Sigma_t^{dec}=0.01^2 I$. When sampling from the transformation likelihood a mask is applied which corresponds to the cone-shaped field-of-view of the ultrasound image.

The mean of the image likelihood is estimated by the sample from the transformation likelihood and applying the transformation on a moving image y M. For this, a spatial transformation module is used. In this example, the first image in the time sequence is used as a moving image. The variance for the image likelihood was fixed to $\sigma_t^2=0.01^2$.

The model is trained end-to-end using importance sampling to maximize the ELBO in (9) by jointly updating all parameters $\{\theta, \varphi, \gamma\}$ in the model. A monotonic annealing schedule weight is used (to the posteriors in the loss function. As an optimizer, Adam is used with exponential decay with factor 0.85 every 20 epoch and an initial learning rate of $10^{-4}$. A batch size of 4 image time series was used, and the model was trained for 50 epochs on a single Nvidia GeForce GTX 1080 Ti graphic card (≈17 hours training).

The results were evaluated using samples from the filtered distribution $x_t \sim p_y(x_t|z_{z:1})$. It was found that the initial model produced transformations where the Jacobian was frequently negative. Therefore, regularization was applied to the displacement field using a Gaussian kernel, $g_\sigma$ $$\hat{\varphi} = \varphi_t * g_\sigma$$

as an alternative version of the model.

The model may be compared with the Demons algorithm (Thirion, 1998). Demons is a popular and fast iterative method for image registration. Since it is iterative, the number of iterations is manually selected. The number of iterations was chosen to be 40. The result was compared with no applied registration to verify the improvements. The average result on the validation data is shown in Table 1:

| Model | info | Avg. Dice ↑ | ↓ % $|J_\varphi| \leq 0$ | GPU (s) ↓ | CPU (s) ↓ |
|---|---|---|---|---|---|
| Our | Filtered | 0.81 ± 0.06 | 2.7% ± 2.7% | 0.09 ± 0.3 · 10⁻² | 0.22 ± 0.5 · 10⁻² |
| Our reg | Filtered | 0.81 ± 0.06 | 0.5% ± 1.0% | 0.09 ± 0.3 · 10⁻² | 0.33 ± 1 · 10⁻² |
| Demons | 40 iterations | 0.81 ± 0.07 | 1.2% ± 1.0% | — | 1.64 ± 2 · 10⁻² |
| None | — | 0.74 ± 0.07 | — | — | — |

The average Dice, percentage of negative Jacobian determinants, and execution time with the Demons algorithm were compared. The time is the average execution time for the entire sequence.

Figure 7:
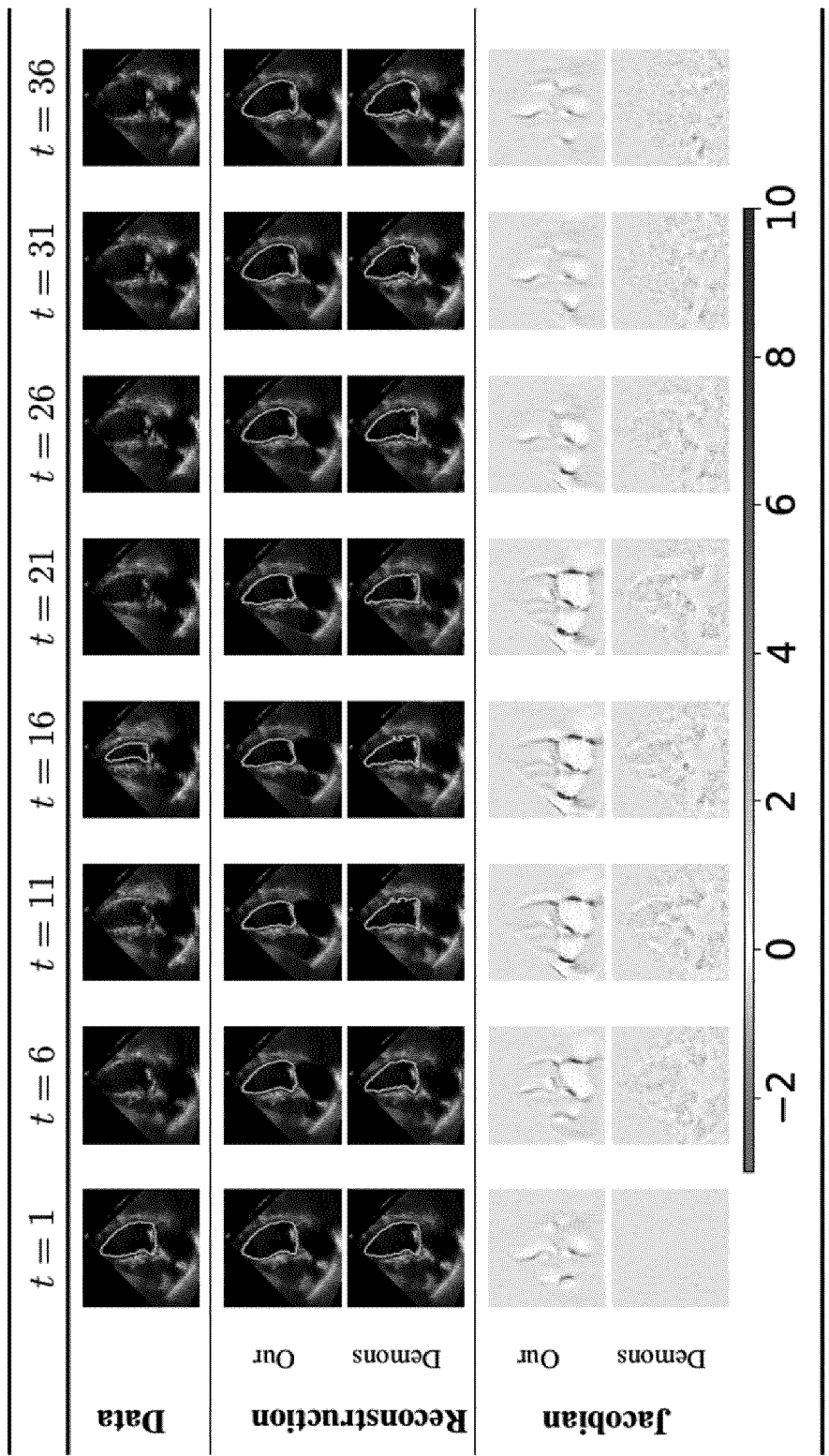
FIG. 7 shows a reconstruction and Jacobian for a one-time sequence using a model according to the present invention.

FIG. 7 depicts the reconstruction and Jacobian for one time sequence using the present model and the Demons algorithm. A segmented region was transferred from one time point, t=1 to the other in the sequence. In this example, the Dice coefficient between the human expert segmentation at t=16 and our estimate is 0.732. The Dice coefficient using Demons algorithm is 0.715. No registration is 0.583.

Figure 8:
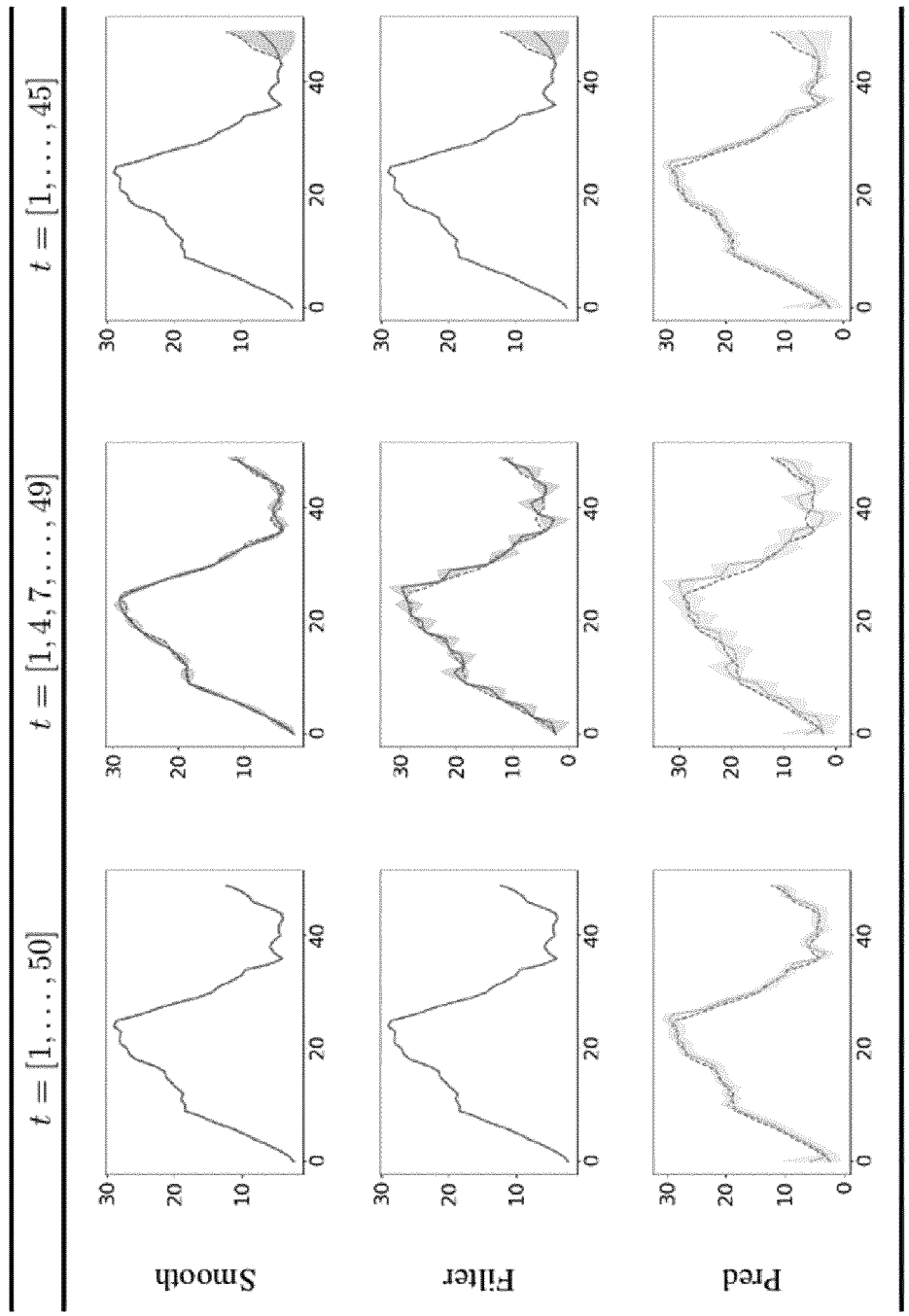
FIG. 8 shows prediction distributions for three examples of input data, when using a model according to the present invention.

From the dynamic in the latent space, w the filtered, smooth, and predictive distributions can be estimated. FIG. 8 shows those estimates for one of the latent space dimensions given three examples of input data: all observed values are known, imputation with every 3rd sample observed and extrapolation for the last 5. A continuous curve is observed, from where it is possible to impute and extrapolate for missing values.

Figure 9:
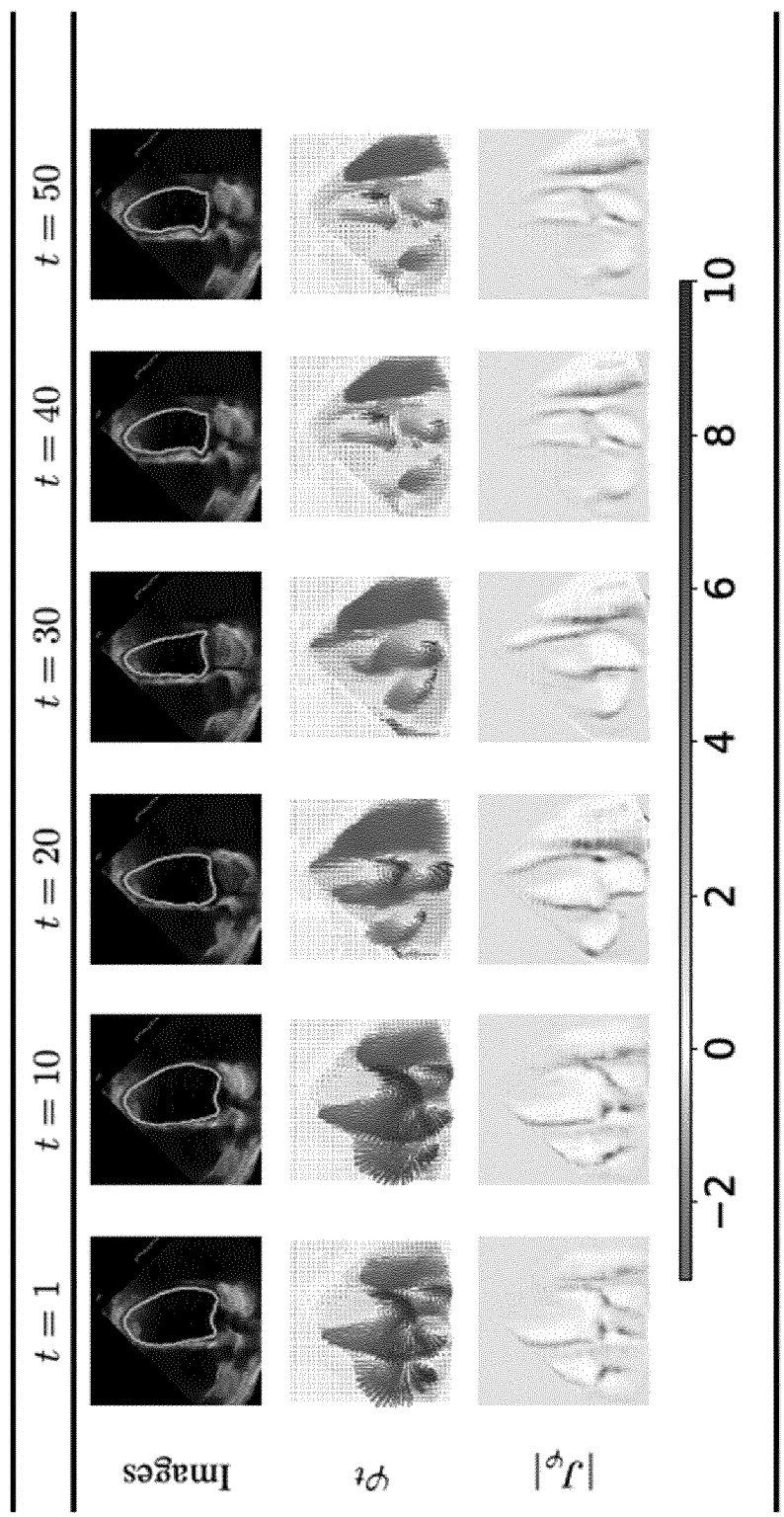
FIG. 9 shows generated transformations when using a model according to the present invention.

The model is generative—given an moving image, $y_M$, a displacement field may be generated by sampling from the initial prior in the latent space and propagating this sample forward in time. FIG. 9 illustrates the generated result for one sample. The transformations are generated by sampling an initial position in the latent space. FIG. 9 shows the transformed moving image (top), the displacement field (middle) and the Jacobian of the generated data (bottom).

FIG. 8 depicts distributions of the smooth, filtered and one-step prediction distribution given observed data for one of the 16 dimensions in the latent observation space. The blue dashed lines are the observed latent variable for the entire sequence, the distributions are represented by their average (solid line), and standard deviation (shaded region).

The present application describes an unsupervised method for extracting latent linear dynamics directly from a medical image time series and discloses how to reconstruct the displacement field from the lower dimensional latent linear dynamic system. With a similar performance in Dice score, the present model outperforms prior methods in speed.

The present application also discloses how to impute missing samples and extrapolate forward in time. Extrapolation support is beneficial for real-time systems, such as radiotherapy devices, when action must be taken given observed data.

Figure 10:
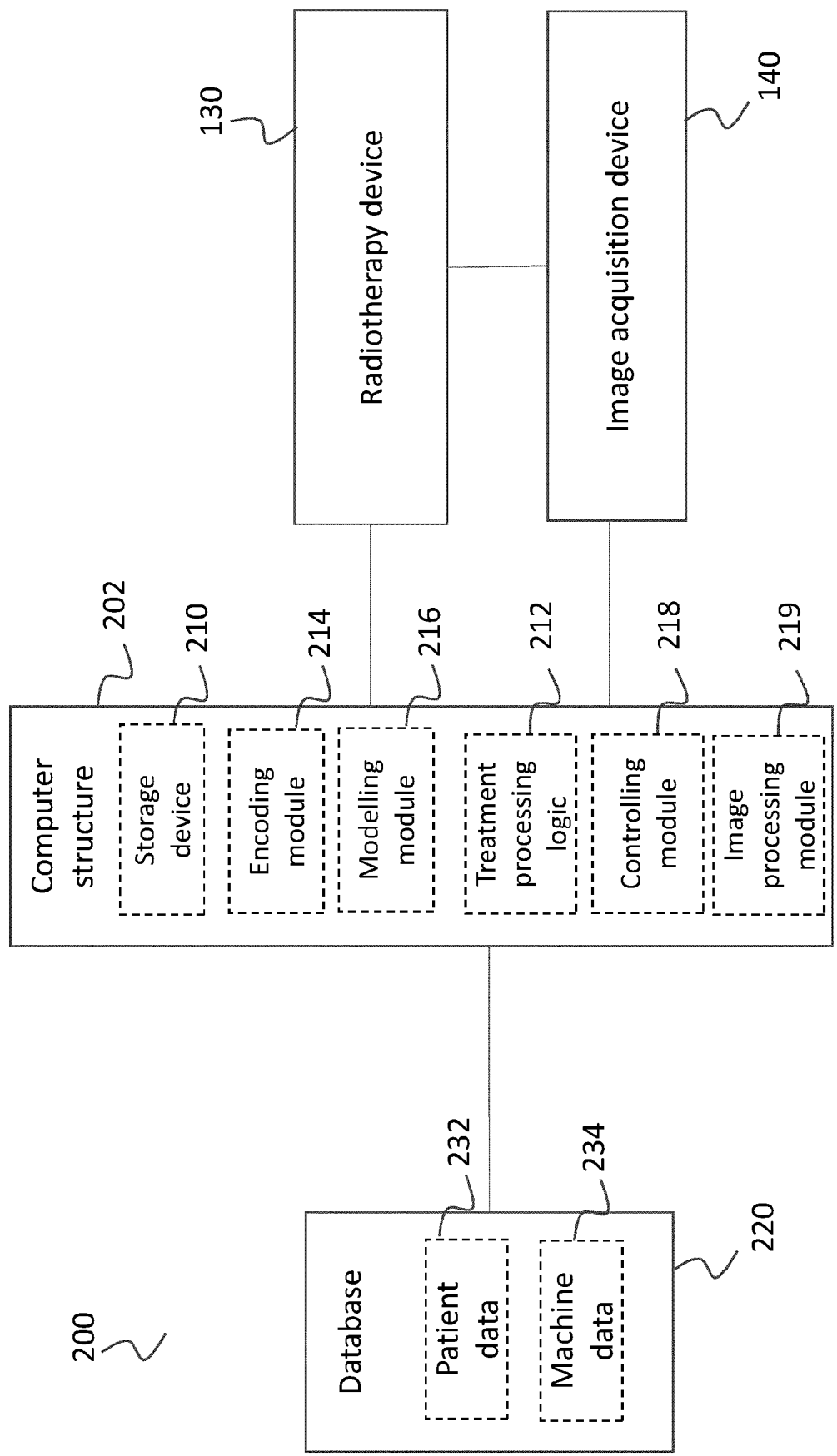
FIG. 10 shows a software structure and system according to embodiments of the present invention.

Turning now to FIG. 10, a computer structure or software 202 in which the methods according to the present invention may be implemented will be described. The computer structure or software 202 may be included in a radiation therapy system 200 as shown in FIG. 10. As shown in FIG. 10, radiation therapy system 200 may include a computer structure 202, a database 220, a radiation therapy device 130 such as a MR linac radiation therapy device, for example, an Elekta Unity® described above with reference to FIG. 1. The computer structure 202 may include hardware and software components to control radiation therapy device 130 including an image acquisition device 140 and/or to perform functions or operations such as treatment planning using a treatment planning software and dose planning using computer structure or software 202, treatment execution, image acquisition, image processing, motion tracking, motion management, or other tasks involved in a radiation therapy process.

The hardware components of computer structure 202 may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMS), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); or other suitable hardware. The software components of computer structure 202 may include operation system software, application software, etc.

In embodiments of the present invention, as shown in FIG. 7, computer structure 202 includes an image processing module 220, for example, executing pre-processing of image data, a storage module 210, an encoding module 212, a modelling module 214, a controller module 216, and treatment processing logic 218.

In embodiments of the present invention, the encoding module 212 is configured to receive a sequence of measurement data of a treatment, and map measurement data to a representation of a treatment geometry. That is, a mapping from the input space X to a latent state space Z is performed. The encoding module may be a machine learning method trained to map an input signal consisting of a sequence of 2D images to a low-dimensional representation of the motion.

In embodiments of the present invention, the modelling module 214 include a state space model configured to model the dynamics of the state space variables in the representation, i.e. how they evolve over time. The state space model may use machine learning to capture the dynamics:

$$z_{t+1} = f(z_0, \ldots, z_t).$$

In one embodiment of the present invention, the representation in a dynamic model describing how variables in the representation evolve over future time points comprises using a linear Gaussian state space model, where the linear Gaussian state space model is:

$$z_{t+1} = Az_t + \varepsilon_t, \varepsilon_t \sim N(0, \sigma^2),$$

In the preferred embodiment of the present invention, the controller module 216 is configured to determine control variables from the state space variables. In embodiments of the present invention, the controller module 216 a linear-quadratic regulator or model-predictive control. The dimensionality of the motion field may differ depending on the intended type of control, e.g. one or two dimensions may suffice for gating and tracking, whereas three dimensions would be appropriate for dose-based adaptation. In other embodiments, a machine learning method for video prediction may include both the encoding module 212 and the modelling module 214. The encoding module 212 and modelling module 214 could either be trained separately or together. An example of the former would be to predict a trajectory in the latent space using Markov chains or Gaussian processes, or to learn a linear model using dynamic mode decomposition. An example of the latter would be to use a Kalman variational auto-encoder trained on sequences of either images or displacement fields.

In embodiments of the present invention, the computer structure 202 can be configured to monitor current patient geometry to calculate dose delivery to a subject (e.g., from one or more MR images) within a given fraction in real time and modify parameters of the radiotherapy device for subsequent doses delivered in the same fraction based on a comparison of the calculated dose delivery to an expected dose delivery specified in a treatment plan by executing instructions or data from the treatment processing logic 218.

In embodiments of the present invention, the treatment processing logic 218 may determine a treatment action for the patient at a defined time point using the estimation from the dynamical model and execute the treatment action at the defined time point. Hence, for example, based on a comparison of the patient anatomy with a predicted patient anatomy, parameters of the radiotherapy device can be adjusted to change an amount of radiotherapy treatment dose delivered at a defined time within a given radiotherapy treatment fraction.

Software 212, 214 and 216 may include computer readable and executable codes or instructions for performing the processes described in detail in this application. For example, a processor device of computer structure 202 may be communicatively connected to a memory/storage device storing software 212, 214, and 216 to access and execute the codes or instructions. The execution of the codes or instructions may cause the processor device to perform operations to achieve one or more functions consistent with the disclosed embodiments.

The software 221, 214, and 216 be configured to execute the methods described herein, for example, the methods described with reference to FIGS. 2-4.

Further, computer structure 202 may be communicatively connected to a database 220 to access data. In some embodiments, database 220 may be implemented using local hardware devices, such as one or more hard drives, optical disks, and/or servers that are in the proximity of computer structure 202. In some embodiments, database 220 may be implemented in a data center or a server located remotely with respect to computer structure 202. Computer structure 202 may access data stored in database 220 through wired or wireless communication.

Database 220 may include patient data 232. Patient data may include information such as (1) imaging data associated with a patient anatomical region, organ, or volume of interest segmentation data (e.g., MRI, CT, X-ray, PET, SPECT, and the like); (2) functional organ modeling data (e.g., serial versus parallel organs, and appropriate dose response models); (3) radiation dosage data (e.g., may include dose-volume histogram (DVH) information); or (4) other clinical information about the patient or course of treatment.

Database 220 may include machine data 224. Machine data 224 may include information associated with radiation therapy device 130, image acquisition device 140, or other machines relevant to radiation therapy, such as radiation beam size, arc placement, on/off time duration, radiation treatment plan data, multi-leaf collimator (MLC) configuration, MRI pulse sequence, and the like.

Image acquisition device 140 may provide medical images of a patient. For example, image acquisition device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, image acquisition device 140 may include an MRI imaging device, a CT imaging device, a PET imaging device, an ultrasound imaging device, a fluoroscopic device, a SPECT imaging device, or other medical imaging devices for obtaining the medical images of the patient.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMS), EPROMs, EEPROMs, magnetic or optical cards, or any type of media suitable for storing electronic instructions, each coupled to a computer system bus.

The order of execution or performance of the operations in embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

Embodiments of the present disclosure may be implemented with computer-executable instructions. The computer-executable instructions may be organized into one or more computer-executable components or modules. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

The invention claimed is:

1. A method for adaptive radiotherapy treatment planning for a patient, comprising:
receiving a sequence of measurement data of the treatment, said measurements being captured at different time points, wherein the sequence of measurement data includes historical measurement data captured before a current treatment session and current treatment data captured during the current treatment session, and wherein the sequence of measurement data includes a sequence of two-dimensional images;
mapping the sequence of measurement data to a representation of a treatment geometry at said time points, wherein the mapping includes mapping the sequence of two-dimensional images to a representation of motion of the treatment geometry;
using the representation in a dynamical model describing how one or more variables in the representation evolve over time;
based on the dynamical model, estimating positions over time of said treatment geometry or one or more selected parts of said treatment geometry;
determining whether a change in position of the treatment geometry meets at least one criterion; and
based on the determining whether the change in position of the treatment geometry meets at least one criterion, determining a treatment action for the patient at a defined future time point using the estimation from the dynamical model.

2. The method of claim 1, further comprising executing the treatment action at the defined future time point.

3. The method according to claim 1, wherein the sequence of measurement data comprises one or more image data sets, said one or more image data sets being captured at a number of different time points.

4. The method according to claim 1, wherein mapping the sequence of measurement data to a representation of a treatment geometry includes:
determining or estimating a displacement field for use in the representation of the treatment geometry, said displacement field describing displacement vectors for a number of points in the current treatment data, each displacement vector specifying a position of a point in reference to a previous position, wherein the determining or the estimating includes tracking a target corresponding to the treatment geometry within a tracking region identified in the measurement data using a feature extractor, wherein the feature extractor is a correlation filter optimized for the tracking region.

5. The method according to claim 1, wherein the treatment geometry includes at least one of a patient anatomy, a radiation therapy system, or one or more parts of the radiation therapy system.

6. The method according to claim 1, wherein estimating positions over time of said treatment geometry or the one or more selected parts of said treatment geometry comprises using the dynamical model to predict a motion of said treatment geometry or selected parts of said treatment geometry at a set of future time points based on the mapping of the sequence of two-dimensional images to the representation of motion of the treatment geometry and using the representation in the dynamical model to describe how the one or more variables in the representation evolves over time, wherein the motion is predicted using one or more of a Markov Chain, a Gaussian process, or a dynamic mode decomposition.

7. The method according to claim 6, wherein determining the treatment action for the patient at the defined future time point using the predicted motion of the treatment geometry over the set of future time points comprises a control policy designed to minimize an average cost over said future time points.

8. The method according to claim 7, wherein said control policy includes optimal control, dynamic programming, approximate dynamic programming or reinforcement learning.

9. The method according to claim 7, wherein said average cost includes a criteria based on at least one of dose or treatment geometry.

10. The method according to claim 1, wherein determining the treatment action for the patient at the defined future time point comprises:

calculating a dose to be delivered to the patient at the defined future time point based on the estimation from the dynamical model and using a cost that includes one or more of a deviation between a planned dose and a desired dose, a difficulty of delivery, or a sensitivity to noise; and adapting a treatment plan based on the calculated dose.

11. The method according to claim 10, wherein executing a treatment action comprises:

selecting a particular treatment plan from among a set of candidate treatment plans; and delivering the calculated dose according to the selected particular treatment plan.

12. The method according to claim 1, wherein determining a treatment action for the patient at a defined future time point comprises:

calculating a dose to be delivered to the patient at a defined point of time based on the estimation from the dynamical model, wherein the estimation from the dynamical model is based on a comparison of the treatment geometry at a current time with a predicted treatment geometry at the future time point; and adapting a treatment plan if a predetermined distance function outputs a distance that exceeds a predetermined threshold, where the distance is computed between the calculated dose and a planned dose to be delivered at the defined point of time.

13. The method according to claim 12, further comprising:

updating a set of candidate treatments plans with the adapted treatment plan.

14. The method according to claim 1, wherein using the representation in a dynamic model describing how the one or more variables in the representation evolve over time comprises using a linear Gaussian state space model.

15. The method according to claim 1, wherein a machine learning model is used in one or more of:

at least a portion of the mapping of the sequence of measurement data to the representation of a treatment geometry at said time points;

using the representation in the dynamical model describing how the one or more variables in the representation evolve over time;

estimating the positions over time based on the dynamical model; or determining the treatment action for the patient at a defined future time point using the estimation from the dynamical model.

16. The method according to claim 15, wherein said machine learning model is a neural network.

17. A non-transitory computer-readable medium having stored therein instructions for a processor, wherein the instructions when read and implemented by the processor of a device for planning adaptive radiotherapy treatment of a patient, cause the processor to:

receive a sequence of measurement data of the treatment, said measurements being captured at different time points, wherein the sequence of measurement data including historical measurement data captured before a current treatment session and current treatment data captured during the current treatment session, and wherein the sequence of measurement data includes a sequence of two-dimensional images;

map the sequence of measurement data to a representation of a treatment geometry at said time points, wherein the mapping includes mapping the sequence of two-dimensional images to a representation of motion of the treatment geometry;

use the representation in a dynamical model describing how one or more variables in the representation evolve over time;

based on the dynamical model, estimating positions over time of said treatment geometry or selected parts of said treatment geometry;

determine whether a change in position of the treatment geometry meets at least one criterion;

based on the determining whether the change in position of the treatment geometry meets at least one criterion, determine a treatment action for the patient at a defined future time point using the estimation from the dynamical model; and send instruction for execution of the treatment action at the defined time point.

18. The non-transitory computer-readable medium of claim 17, wherein the sequence of measurement data comprises one or more image data sets, said one or more image data sets being captured at number of different time points.

19. A method for adaptive radiotherapy treatment planning for a patient, comprising:

receiving a sequence of measurement data of the treatment, wherein measurements included in the sequence of measurement data is captured at different time points, wherein the sequence of measurement data including historical measurement data captured before a current treatment session and current treatment data captured during the current treatment session, and wherein the sequence of measurement data includes a sequence of two-dimensional images;

mapping the sequence of measurement data to a representation of a treatment geometry at the time points, wherein the mapping includes mapping the sequence of two-dimensional images to a representation of motion of the treatment geometry;

using the representation in a dynamical model describing how one or more variables in the representation evolve over time;

based on the dynamical model, estimating positions over time of the treatment geometry or one or more selected parts of the treatment geometry, wherein the estimating comprises using the dynamical model to predict a motion of the treatment geometry or selected parts of the treatment geometry over a set of future time points based on the mapping of the sequence of two-dimensional images to the representation of motion of the treatment geometry and using the representation in the dynamical model to describe how the one or more variables in the representation evolves over time, wherein the motion is predicted using one or more of a Markov Chain, a Gaussian process, or a dynamic mode decomposition;

determining whether a change in position of the treatment geometry meets at least one criterion;

based on the determining whether the change in position of the treatment geometry meets at least one criterion, determining a treatment action for the patient at a defined future time point using the estimation from the dynamical model, wherein determining the treatment action for the patient at the defined future time point uses the predicted motion of the treatment geometry or selected parts of the treatment geometry over the set of future time points comprises a control policy designed to minimize an average cost over the set of future time points, and wherein the control policy includes optimal control, dynamic programming, approximate dynamic programming or reinforcement learning; and executing the treatment action at the defined future time point.

20. The method according to claim 19, wherein determining the treatment action for the patient at the defined future time point comprises:

calculating a dose to be delivered to the patient at the defined future time point based on the estimation from the dynamical model and using a cost that includes one or more of a deviation between a planned dose and a desired dose, a difficulty of delivery, or a sensitivity to noise; and adapting a treatment plan based on the calculated dose.

* * * * *